Figure 1A:
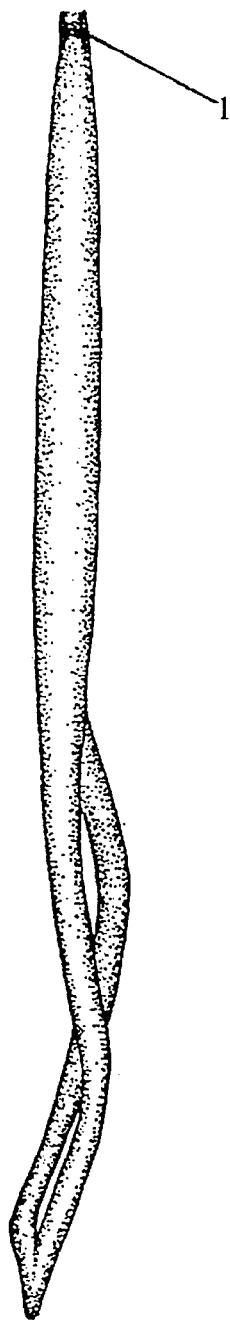

US005645819A

United States Patent [19]
Klapow

[11] Patent Number: 5,645,819
[45] Date of Patent: Jul. 8, 1997

[54] METHODS OF DIAGNOSING AND TREATING AN INTESTINAL AND LUNG ROUNDWORM INFECTION

[76] Inventor: Lawrence A. Klapow, 1010 Park Ave., Burlingame, Calif. 94010

[21] Appl. No.: 403,278

[22] Filed: Mar. 13, 1995

[51] Int. Cl.$^6$ .................................................. A61K 9/12

[52] U.S. Cl. .............................................. 424/45; 424/405

[58] Field of Search ....................................... 424/405, 45

[56] References Cited

U.S. PATENT DOCUMENTS

| | | | |
|---|---|---|---|
| 3,956,499 | 5/1976 | Gyurik et al. | 424/405 |
| 5,118,673 | 6/1992 | Carpenter et al. | 514/54 |

OTHER PUBLICATIONS

*Medical Microbiology—An Introduction to Infectious Diseases,* John C. Sherris ed, Ch. 44 (James J. Plorde, "*Introduction to Pathogenic Parasites* "), Elsevier Science Publishing Co., New York, NY (1984).

Edward K. Markell & Marietta Voge, *Medical Parasitology,* Ch. 2, W.B. Saunders Co., Philadelphia, PA (5th ed. 1981).

J. Walter Beck & John E. Davies, *Medical Parasitology,* Ch. 8, The C.V. Mosby Co., Saint Louis, MO (2d ed. 1976).

*Medical Microbiology—An Introduction to Infectious Diseases,* John C. Sherris ed., Ch. 49 (James J. Plorde, *"Intestinal Nematodes"*), Elsevier Science Publishing Co., Inc., New York, NY (1984).

*AHFS Drug Information 94,* Gerald K. McEvoy, ed., pp. 39–41 (and see pp. 41–54) (1994).

American Medical Association Drug Evaluation, Annual 1994, Strongyloidiasis, pp. 1742, 1751–1752.
L. von Kuster & R. Genta, "Cutaneous Manifestations of Strongyloidiasis, " Arch Dermatol 124:1826–30 (1988).

A.R. Maggenti, *Encyclopedia of Science and Technology: Nemata,* 11:616–20, McGraw Hill (1994).

G.W. Stamm et al. *Veterinary Guide For Farmers,* p. 169, Hearst Corp, New York, NY (1975).

D.L. Lee, *The Physiology of Nematodes,* p. 117, W.H.Freeman Co., San Francisco, CA (1963).

R.C. Anderson, *Nematode Parasites of Vertebrates, Their Development and Transmission,* C.A.B. International (1992).

L.R. Ash and T.P. Oribel, *Atlas of Human Parasitology,* American Society of Clinical Pathologists, Chicago, IL (3rd ed. 1990).

N.D. Levine, *Nematode Parasites of Domestic Animals and of Man,* Burgess Pub. Co., Minneapolis, MN (1968).

K.I. Skryabin et al., *Key to the Parasitic Nematodes: vol. 3, Strongylata* K.I. Skryabin ed., E.J. Brill Pub., New York, N, pp. 574–575, pp. 842–843 (1992).
M.C. Durette–Desset, "Trichostrongyloid Nematodes and Their Vertebrate Hosts: Reconstruction of the Phylogeny of a Parasitic Group, " Advances in Parasitology 24:239–307 (1985).

M.C. Durette–Desset and A.G. Chabaud, "Sur Les Molineinae Parasites De Mammiferes, " *Annales de Parasitologie* (Paris)456(5):489–502 (1981).

L.X. Liu & P.F. Weller, "Strongyloidiasis and Other Intestinal Nematode Infections, " Infectious Disease Clinics of North America, Parasitic Diseases 7(3):655–82 (1993).
R. Genta, "Global Prevalence of Strongyloidiases: Critical Review With Epidemiologic Insights into Prevention of Disseminated Disease, " Rev. Infect Dis 11(2):755–67 (1989).

(List continued on next page.)

*Primary Examiner*—Raj Bawa
*Attorney, Agent, or Firm*—Medlen & Carroll

[57] ABSTRACT

Methods for the diagnosis and the treatment of *Cryptostrongylus pulmoni*, a heretofore unrecognized microscopic roundworm, are described. The roundworm's unique life cycle prevents diagnosis by traditional stool analysis methods. The methods for diagnosis and treatment entail the administration of an aerosolized formulation of an anthelmintic agent. Additionally, the invention describes a new composition of thiabendazole, a known anthelmintic agent, for aerosolized administration that can be used for diagnosing and treating the infection caused by the roundworm.

6 Claims, 4 Drawing Sheets

Hookworms (*Necator americanus; Ancylostoma duodenale*)

Threadworm (*Strongyloides stercoralis*)

Human Lungworm (*Cryptostrongylus pulmoni*)

OTHER PUBLICATIONS

Physician's Desk Reference, 45th Ed. (see particually pp. 1464–1465) (1991).

A.E. Klein, *The Parasites We Humans Harbor*,Ch. 3, Elsevier/Nelsom Books, New York, NY pp. 100–101 (1981).

G.P. Holmes, et al., "Chronic Fatigue Syndrome: A Working Definition, " Ann Intern Med 108:387–89 (1988).

R. Hegner et al., *Outlines of Medical Zoology*, Macmillan, New York, NY pp. 66–67 (1927).

D.S. Bell, *The Doctors Guide to Chronic Fatigue Syndrome*, Addison–Wesley Pub. pp. 58–61 (1994).

K.H. Berne, *Running On Empty: Chronic Fatique Immune Dysfunction Syndrome*, Hunter House Inc., Alameda, CA pp. 40–43 (1992).

A.A. Poltera & N. Katsimbura, "Granulomatous Hepatitis Due to *Strongyloides Stercorolis*,, " J Path 113:241–46 (1973).

A.R. Lloyd et al., "Immunological Abnormalities in the Chronic Fatigue Syndrome," Med J. Aust 151(3):122–24 (1989).

N.G. Klimas et al., "Immunological Abnormalities in the Chronic Fatigue Syndrome, " J Clin Microbiol 28:1403–10 (1990).

M.B. Yunus, *Chronic Fatigue Syndrome and Fibromyalgia: Similarities and Differences*, Pub. CFIDS Ass Am, Charlotte, NC 7 pps (1994).

*Immunology and Molecular Biology of Parasitic Infections*, Kenneth S. Warren ed., Ch. 19 (1993).

K. Koga et al., "A modified agar plate for detection of *Strongyloides stercoralis*. " Am J Trop Med Hyg 45(4):518–21 (1991).

D.I. Pritchard, "Immunity to Helminths: Is Too Much IgE Parasite–Rather Than Host–Protective?" Parasite Immunology, 15:5–9 (1993).

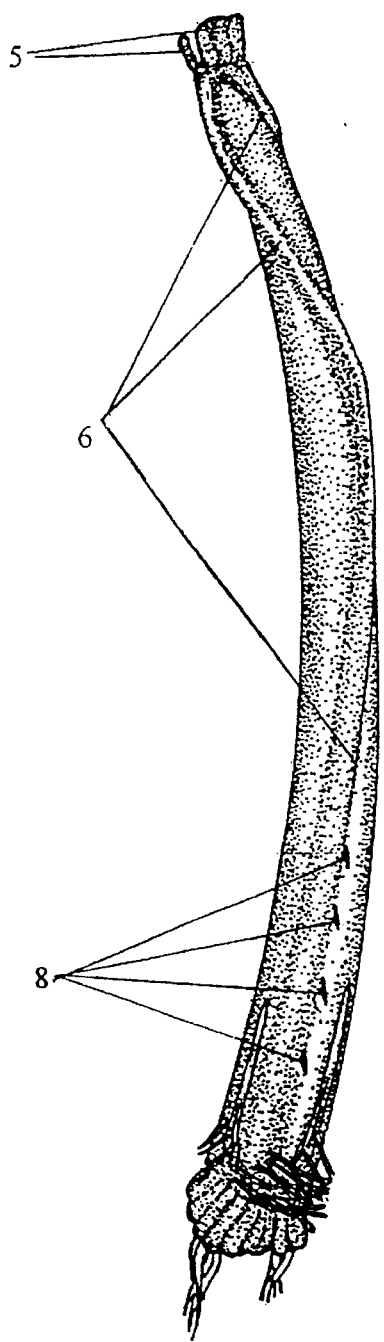
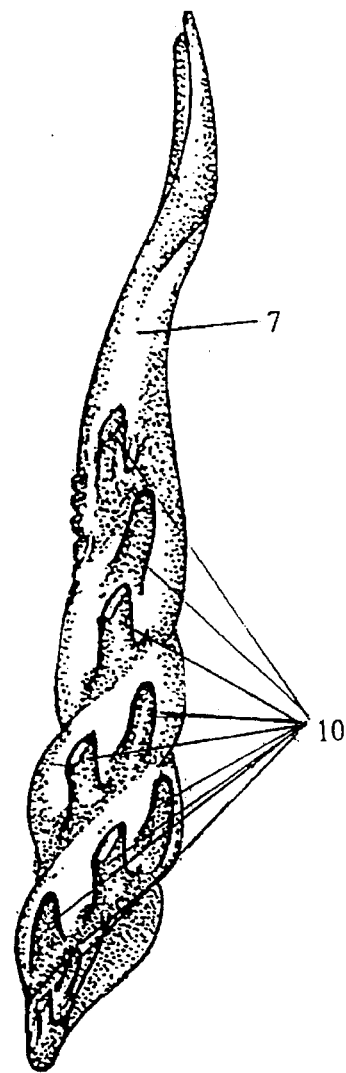
FIGURE 1C
FIGURE 1D

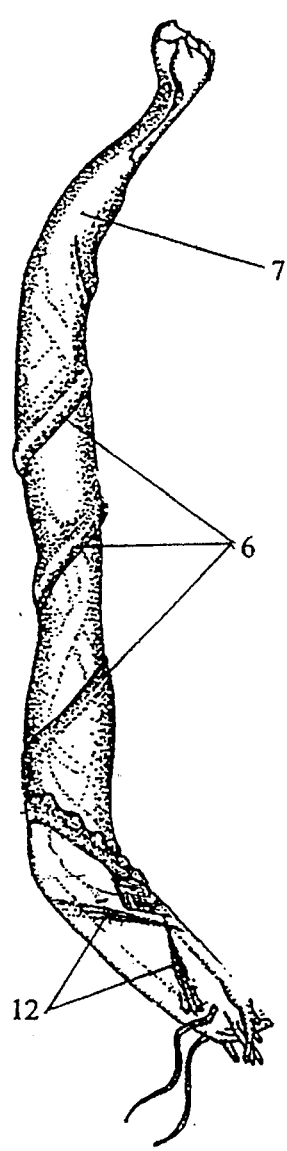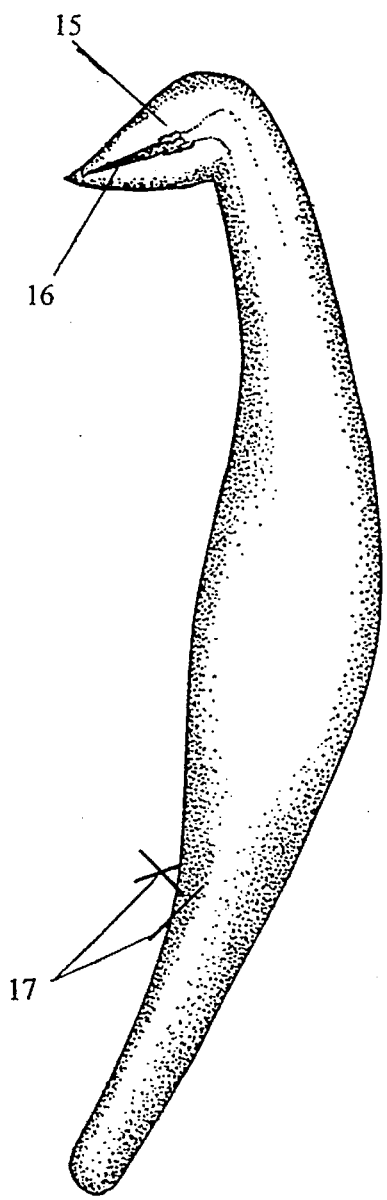
FIGURE 1E
FIGURE 1F

METHODS OF DIAGNOSING AND TREATING AN INTESTINAL AND LUNG ROUNDWORM INFECTION

FIELD OF THE INVENTION

The invention relates to the diagnosis and treatment of a parasitic infection and particularly to the preparation and administration of a pharmaceutical preparation to diagnose and treat a heretofore unrecognized roundworm.

BACKGROUND OF THE INVENTION

Though most prevalent today in developing third-world countries, parasitic infections plague industrialized countries as well. Parasitic infections may not be as common as infections of bacterial and viral origin, but they can cause tremendous human suffering.

Numerous types of parasitic infections are treated each year in the United States, with toxoplasmosis, giardiasis, trichomoniasis, and pinworm infections among the most frequently encountered. [See generally, *Medical Microbiology—An Introduction to Infectious Diseases*, John C. Sherris ed., Ch. 44 (1984)]. Immunocompromised patients, such as Acquired Immune Deficiency Syndrome (AIDS) sufferers, are especially susceptible to certain types of parasitic infections.

The term "parasitism" denotes a relationship wherein a host organism is harmed in some way by the activities of another organism, the parasite. Thus, parasitism is distinguishable from other relationships where both organisms benefit (mutualism) or where one organism benefits and the other organism is not harmed (commensalism). Parisitism entails a prolonged and intimate relationship between the involved organisms. [See generally, Edward K. Markell & Marietta Voge, *Medical Parasitology*, Ch. 2 (5th ed. 1981)].

The intestinal roundworms represent one classification of parasites. The intestinal roundworms are also referred to as the intestinal nematodes; hence, the two terms may be used interchangeably. The details of the intestinal roundworms' structural characteristics and reproductive properties are well known. [See, e.g., J. Walter Beck & John E. Davies, *Medical Parasitology*, Ch. 8 (2d ed. 1976); *Medical Microbiology—An Introduction to Infectious Diseases*, Ch. 49, supra; and Edward K. Markell & Marietta Voge, Medical Parasitology, Ch. 8, supra].

Six intestinal roundworms have traditionally been recognized as infecting humans, affecting about 25% of the world's population. These intestinal roundworms are *Enterobius vermicularis* (the pinworm), *Trichuris trichuria* (the whipworm), *Ascaris lumbricoides* (the large roundworm), *Necator americanus* and *Ancyclostoma duodenale* (the hookworms), and *Strongyloides stercoralis*. The adult forms of each can persist for years in the lumen of the human gut, and the severity of illness produced from these intestinal roundworms is dependent upon their extent of adaptation to the human host. The manifestations of intestinal roundworm infection include malnutrition, anemia, gastrointestinal disturbances, and even death. [See *Medical Microbiology—An Introduction to Infectious Diseases*, Ch. 49, supra].

The modalities used to treat roundworm infection primarily involve oral administration of a pharmaceutical agent. Several oral agents are available in the United States to treat roundworm infections, including mebendazole (Vermox®, Janssen), piperazine citrate, pyrantel pamoate (Antiminth®, Pfizer), and thiabendazole (Mintezol®, Merck).

Most pharmaceutical agents are effective against more than one species of roundworm, though different treatment regimens are often employed against different organisms. To illustrate, mebendazole can be used to treat both pinworm infection and hookworm infection (as well as infections caused by other roundworms). The regimen for treating pinworm infection (enterobiasis) generally entails administration of a single 100 mg dose; some clinicians suggest administration of a second 100 mg dose two weeks later. By comparison, treatment of hookworm infection usually is performed by administration of 100 mg given twice daily for three consecutive days; this regimen is repeated if the patient is not cured within 3–4 weeks. Thus, though the same drugs are often effective against several types of roundworms, different treatment regimens are frequently required. [See generally, *AHFS Drug Information 94*, Gerald K. McEvoy, ed., pp.39–41 (1994)].

Numerous adverse effects have been reported following administration of pharmaceutical agents used to treat roundworm infections. Though the newer agents generally are associated with fewer and less severe adverse effects, the adverse effects experienced with these newer agents still can interfere with the subject's normal functioning. For example, diarrhea, abdominal pain, nausea, vomiting, dizziness, drowsiness, and weakness, among others, have all been reported with mebendazole, an agent generally recognized as causing minimal adverse effects.

Finally, the anthelmintic agents have not eliminated parasitic infections as a health concern, even in developed countries like the United States. Again, to use mebendazole as an example, egg reduction percentages and/or cure rates of over 90% are generally achieved in patients suffering from enterobiasis, ascariasis, and certain species of hookworm infection. Similar egg reduction rates, as well as cure rates of about 70%, have been produced by mebendazole treatment in whipworm infection (trichuriasis). Thus, even when a roundworm has been identified and the concomitant drug-of-choice has been administered, it is still uncertain whether all vestiges of the infection will be eliminated.

Though the treatment modalities currently being utilized to combat parasitic infections have had some success, they have not eradicated parasitic infections. Furthermore, individuals are sometimes intolerant to pharmaceutical agents that are generally effective against the organism they harbor. Individuals may also suffer from infections caused by parasites that are not susceptible to any presently available treatment modality. Clearly, new treatment methods and agents would be welcomed by those plagued by parasitic infections who either cannot tolerate available treatment regimens or who harbor resistant organisms.

SUMMARY OF THE INVENTION

The invention describes methods for the diagnosis and the treatment of a heretofore unrecognized microscopic roundworm. The roundworm's unique life cycle has prevented diagnosis by traditional stool analysis methods. The diagnostic and treatment methods entail the administration of an aerosolized formulation of an anthelmintic agent. Additionally, the invention describes a new composition of a known anthelmintic agent for diagnosing and treating the infection caused by the roundworm. The subject's clinical history and potential clinical manifestations of the roundworm infection are also presented to assist in fully understanding the invention.

Specifically, the invention contemplates a method of diagnosing the presence of roundworms, comprising the steps of: (a) providing i) a subject suspected of being infected with roundworms and ii) an effective amount of an anthelmintic agent for inhalation; (b) administering the effective amount of the anthelmintic agent by inhalation to the subject; (c) collecting sputum samples from the subject following administration; and (d) analyzing the sputum samples for the presence of the roundworms.

In addition, the invention contemplates the aforementioned diagnostic method wherein the roundworms have a lifecycle such that they are not detectable in feces. In some embodiments, the roundworms are *Cryptostrongylus pulmoni*.

Furthermore, the present invention contemplates the aforementioned diagnostic method wherein the anthelmintic agent is thiabendazole. When the anthelmintic agent is thiabendazole, some embodiments of the invention contemplate administering that pharmaceutical agent in a daily dose ranging between approximately 25 mg and 210 mg. In other embodiments, thiabendazole is administered in a daily dose ranging between approximately 35 mg and 150 mg.

The present invention also contemplates a method of treating a roundworm infection, comprising the steps of: (a) providing i) a subject infected with roundworms and ii) an effective amount of an anthelmintic agent for inhalation; and (b) administering an effective amount of the anthelmintic agent by inhalation to the subject, thereby treating the roundworm infection.

Additionally, the present invention contemplates the aforementioned treatment method wherein the roundworms have a lifecycle such that they are not detectable in feces. In some embodiments, the roundworms are *Cryptostrongylus pulmoni*.

Moreover, the present invention contemplates the aforementioned treatment method wherein the anthelmintic agent is thiabendazole. When the anthelmintic agent is thiabendazole, some embodiments of the invention contemplate administering that pharmaceutical agent in a daily dose ranging between approximately 25 mg and 210 mg. In other embodiments, thiabendazole is administered in a daily dose ranging between approximately 35 mg and 150 mg.

Finally, the present invention contemplates an aerosolized anthelmintic solution, comprising a sterile liquid vehicle and thiabendazole dissolved in the sterile liquid vehicle. In some embodiments, the sterile liquid vehicle comprises sterile water for injection and an acidic pH-modifying substance in an amount sufficient to adjust the pH of the solution to between approximately 3.5 and 4.0, and preferably approximately 4.0. In some embodiments of the present invention, the aerosolized anthelmintic solution has a concentration of thiabendazole ranging between approximately 1 mg/ml and 2 mg/ml.

DEFINITIONS

To facilitate understanding of the invention set forth in the disclosure that follows, a number of terms are defined below.

The term "anthelmintic" refers to an agent that destroys or expels intestinal roundworms.

The term "effective amount" refers to that amount of an anthelmintic agent that is required to produce a desired effect. The effect desired herein is either the diagnosis or the treatment of a roundworm infection. The effective amount of an anthelmintic agent generally depends on the characteristics of the subject who is to receive the agent, including the type of roundworm involved, the severity of the roundworm infection, the immune status of the subject, and the weight of the subject. Typically, the effective amount of thiabendazole when taken by inhalation is in the range from 25 mg to 210 mg.

The term "solution" refers to a liquid composition wherein there is a mingling together of two or more substances without the occurrence of a reaction by which the substances would lose their individual properties.

The term "liquid vehicle" refers to a liquid substance or excipient, with or without therapeutic action, used as a medium for the administration of a therapeutically active agent such as a pharmaceutical agent.

The term "pH-modifying substance" refers to a substance that is added to a solution to either make the solution more acidic (i.e., decrease the pH) or make the solution more alkaline (i.e., increase the pH). A pH-modifying substance may be useful in making a solution more physically stable or more tolerable to a subject, among other things. A preferred pH-modifying substance is hydrochloric acid.

The term "subject" includes humans as well as animals.

DESCRIPTION OF THE DRAWINGS

FIG. 1A depicts a cuticle cast of the fourth-stage larva of *Cryptostrongylus pulmoni* (n.gen., n.sp.).

FIG. 1B depicts a mature female of *C. pulmoni* (n.gen., n.sp.).

FIG. 1C depicts a mature male of *C pulmoni* (n.gen., n.sp.).

FIG. 1D depicts a first-stage ("gripper") larva of *C. pulmoni* (n.gen., n.sp.).

FIG. 1E depicts a second-stage ("swimmer") larva of *C. pulmoni* (n.gen., n.sp.).

FIG. 1F depicts a third-stage ("climber") larva of *C. pulmoni* (n.gen., n.sp.).

FIG. 2 illustrates the general life cycle schemes of human hookworms (*Necator americanus* and *Ancylostoma duodenale*) and threadworm (*Strongyloides stercoralis*) in comparison to the newly identified hidden lungworm (*C. pulmoni* (n.gen., n.sp.)).

DESCRIPTION OF THE INVENTION

The invention relates to the diagnosis and treatment of a parasitic infection and particularly to the preparation and administration of a pharmaceutical preparation to diagnose and treat a heretofore unrecognized roundworm.

Though the preparation and administration of a pharmaceutical preparation is the crux of the invention, an understanding of the subject's illness and various characteristics of the newly discovered roundworm is required to fully appreciate the invention. To that end, the description of the invention is divided into the following parts: I) Clinical History of the Patient; II) Characteristics of *Cryptostrongylus pulmoni* (n.gen., n.sp.); III) Pharmaceutical Preparation And Delivery; and IV) Potential Clinical Manifestations Of Human *C. pulmoni* (n.gen., n.sp.) Infection.

I. Clinical History of the Subject

An unusual microscopic roundworm was isolated from the sputum of a 50 year old male subject. The subject suffered from a relapsing multi-systemic illness, with exacerbated allergies and hypersensitivity reactions which began 19 years ago in a series of prostrating flu-like attacks. The subject's disease has been diagnosed as Chronic Fatigue Syndrome. The subject had a history of moderately severe childhood allergies and asthma, and the allergies persisted to a lesser degree into adulthood, triggered by house dust, pollens, and animal dander allergens.

Following the sudden onset of the flu-like illness, the subject's symptoms became much more intense and widespread, with headaches, chills, joint pain, muscle pain, weakness, shortness of breath, frequent and severe gastrointestinal symptoms, cognitive difficulties, and other debilitating manifestations. Furthermore, the subject began to react to a much wider range of materials, eventually developing sensitivities to various foods, molds, and common household and workplace chemical products.

The subject also had prominent and persistent skin rashes on his buttocks and upper thighs. The skin rashes entailed scattered erythematous macular papular spots which also occurred to a lesser degree on other parts of the subject's body; individual erythematous papillae required several months to heal. In addition, the subject had prominent petechial rashes on his buttocks composed of up to four sequential subcutaneous hemorrhages, giving the appearance of a dotted line. Such rashes are seen in threadworm infections [See eg., American Medical Association Drug Evaluation Annual 1994. Strongyloidiasis, pp. 1742–43] and are thought to indicate autoinfectious processes (see below). [See generally, von Kuster & Genta, "Cutaneous Manifestations of Strongyloidiasis," Arch Dermatol 124:1826–30 (1988)]. Because of these skin signs, the subject was thought at one time to have a threadworm infection. The subject underwent extensive testing to identify any evidence of threadworm or other known roundworm infection. These tests included four series of microscopic stool examinations, two strongyloides antibody tests (Strongyloides IgG antibody), and twenty-five live-culture tests over a two-year period; all of the test results were negative.

Avoidance and other means of controlling exposure to symptom-triggering substances (mainly diet and antifungal therapies) were successful to varying degrees in relieving the subject's most debilitating symptoms. The subject was able to work full-time for most of his long illness, although the subject was forced to accept significant changes in work duties and schedule. However, as the subject's illness progressed significantly, the subject had to stop working. Thereafter, the subject began an intensified search for the underlying cause of the intractable progressing illness. That search resulted in the discovery of a new species of lung and intestinal nematode pathogen, which the subject named "*Crylptostrongylus pulmoni*" (n.gen., n.sp.), or "hidden lungworm."

II. Characteristics of *Cryptostrongylus Pulmoni* (n. gen., n.sp.)

A. Overview

*C. pulmoni* (n.gen., n.sp.) is a deeply hidden parasite which is virtually undetectable without specific knowledge of its unique life cycle. The principal diagnostic difficulty results from the fact that no eggs or larvae are deposited in expelled feces, in contrast with all other known intestinal roundworm parasites. [See generally, *Medical Microbiology—An Introduction to Infectious Diseases*, Ch. 44, supra]. *C. pulmoni* (n.gen., n.sp.) larvae, after feeding in the intestinal mucosa, migrate through the abdominal organs, eventually entering a blood vessel which takes them to the lungs. They sexually mature and reproduce in the lungs, giving rise to larval forms which initially feed in the lungs; thereafter, the larvae traverse the trachea and esophagus to re-enter the digestive track or are expelled through the oral/nasal passages.

Larvae and sexually mature forms of *C. pulmoni* (n.gen., n.sp.) have been found in the sputum only after administration of the anthelmintic thiabendazole (Mintezol®). It is the presence of *C. pulmoni* (n.gen., n.sp.) in the sputum that provides a clinical basis for identifying *C. pulmoni* (n.gen., n. sp.) infection. Since neither eggs nor larvae exit via feces, stool examinations and stool culture methods are negative. Hence, the clinical methods traditionally employed for detecting intestinal roundworms—microscopic stool examination and stool culture techniques—are ineffective. In addition, *C. pulmoni's* (n.gen., n.sp.) extremely small size (about 0.20–0.80 mm long), unusual appearance, apparent low reproductive rate, and the need to pre-administer a strong anthelmintic drug (e.g., thiabendazole) to routinely recover any specimens, provide further analytical difficulties which have caused this roundworm species to escape detection until now.

It should be noted that *C. pulmoni* (n.gen., n.sp.) apparently has autoinfective capability similar to that of the human threadworm *Strongyloides stercoralis*. Autoinfection is a process of self-infection. It entails a new infective cycle with production of a new generation of larvae and adults. Autoinfection may be of two types, external and internal. In external autoinfection, infective filariform larvae that have been extruded from the subject's rectum invade the subject's perianal skin without an intervening soil phase. Internal autoinfection is distinguishable from external autoinfection in that the infective filariform larvae are still within the subject's body when they invade the subject's intestinal mucosa and begin a new cycle of infection. [See generally, *Medical Microbiology—An Introduction to Infectious Diseases*, Ch. 44, supra].

Since autoinfection allows for reproductive expansion of the parasite population, it is important not to upset the balance between host and parasite. This balance can be upset with the prolonged administration of immune-suppressing therapies, such as treatment with the corticosteroids. When *S. stercoralis* is involved, the ensuing acceleration of the autoinfective process which increases and disseminates the host's worm burden can be fatal. [See Genta, supra]. Even if the autoinfective process of *C. pulmoni* (n.gen., n.sp.) is determined to be less prolific than that of *S. stercoralis*, patients and practitioners should be mindful of the possibility of encouraging the growth of *C. pulmoni* (n.gen., n.sp.) with the administration of immune-suppressing therapies over long periods of time.

B. Detailed Description and Interpretation of Specimens Recovered in Sputum

Even with administration of thiabendazole to the subject, the yield of recovered specimens was very low. The description of each parasitic life stage that follows is based on a few specimens and may reflect to some degree the circumstances surrounding the preservation of the specimens (See Example 1 in the Experimental section, infra). These samples, when taken within the context of the subject-host's symptoms and medical history, provide the basis for developing a schematic of the organism's life cycle.

The general intestinal roundworm life cycle involves four larval stages leading up to reproductive adults. [See Maggenti, *Encyclopedia of Science and Technology: Nemata*, 11:616–20 (1994)]. Evidence of all four larval stages and adults for *C. pulmoni* (n.gen., n.sp.) was found in the sputum samples obtained from the subject.

The six specimens depicted in FIGS. 1A through 1F represent the life cycle sequence of *C. pulmoni* (n.gen., n.sp.). The specimen in FIG. 1A is the cuticle cast of a larval worm approximately 700 microns long. A thickened reinforcing ring 1 at its anterior suggests that it is capable of boring through tissue. This specimen is thought to be the molt of a filariform larval stage which originated in the host's intestine and proceeded to the lungs via the venous circulation. Fourth stage filariform larvae molt into sexually mature adults.

Figure 1B:
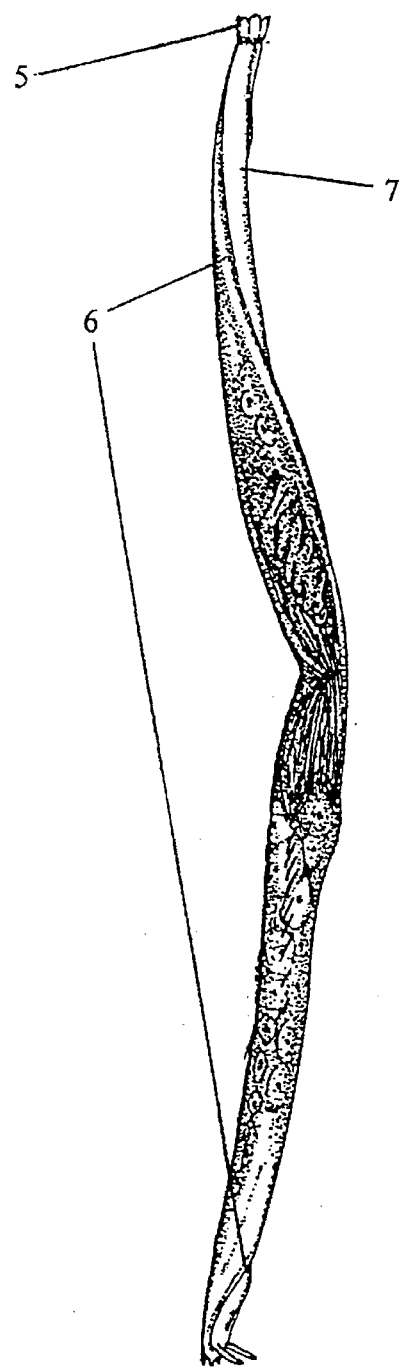

The specimens depicted in FIG. 1B and 1C represent, respectively, a female (approximately 700 microns long) and a male (approximately 300 microns long). Both sexes have small lips 5 and thick cuticles 7, with ridges 6 which spiral around the long axis of the body. These characteristics suggest an affinity with the "twisted wireworm" parasites of domestic and wild mammals. [See Stamm et al., *Veterinary Guide For Farmers*, p. 169 (1975)]. The cuticle is very opaque and ornamented with small surface markings 8 (visible in FIG. 1C), set diagonally to the spiral ridges.

The specimen shown in FIG. 1D is a first-stage larva. It is approximately 200 microns long and has large, projections 10 emanating from the spiraled cuticle 7. The shape of the projections 10 are either axe-like or finger-like. They serve as anchoring devices to prevent the larvae from being expelled from the lung.

The specimen depicted in FIG. 1E is about 400 microns long, and represents a second-stage larva. Its cuticle 7 has a glass-like translucence and is marked by prominent spiral ridges 6. Furthermore, the specimen's broad tail with distinctive juxtaposed muscle groups 12 suggests that it is capable of swimming. This larva is thought to be a mobile swimming form of *C. pulmoni* (n.gen., n.sp.) which forages on the wet surfaces of the interior lung tissue.

The final specimen depicted in FIG. 1F is highly unusual. It appears distinct from all known human worm parasites. Its structure and apparent function make sense biologically in terms of the life cycle of *C. pulmoni* (n.gen., n.sp.). Furthermore, morphological analogs are known to exist in the nematode phylum, although these analogs occur in free-living rather than parasitic forms. It is proposed that this specimen is a third-stage larva specially adapted to crawl up vertical surfaces. The special adaptations for climbing include a bent head 15 with a pick-like stylus 16 and bristles 17 on the ventral-posterior surface presumably used for traction. The third-stage larva is normally the infective form in most roundworms. Upon entering the throat, the third-stage "climber" larva of *C. pulmoni* (n.gen., n.sp.) is either expelled in sputum or swallowed. If it is swallowed, it enters the intestine and molts into a fourth-stage larva, thereby completing the auto-infective process.

It is not uncommon for roundworms to possess climbing adaptations. Marine stiltworm nematodes as well as other free-living forms have both anterior and posterior adhesive structures which allow them to crawl up steep vertical surfaces in an inchworm-like "looping" fashion. [See generally, Lee, *The Physiology of Nematodes*, p 117 (1963)]. It should be noted that the specimen depicted in FIG. 1F may be damaged. The specimen originally appeared, on cursory viewing, to have more than one row of bristles which were lost when the specimen was manipulated further.

Finally, the presence of both sexes and evidence for all four larval forms in sputum indicates that sexual reproduction of *C. pulmoni* (n.gen., n.sp.) takes place in the lungs. No eggs where found in the sputum. The female is viviparous and gives birth to live young. The presence of these specimens in sputum along with the previously noted symptoms and skin signs indicates that this species of roundworm is capable of reproducing and re-infecting its human host through a cycle of autoinfection, previously alluded to, involving migration between the host's respiratory and digestive tracks. It can therefore produce chronic infection, as evidenced by the subject's infection which dates back almost twenty years.

C. Taxonomy of *C. pulmoni* (n.gen., n.sp.)

The recovered specimens were examined by a nematode specialist who placed the species in the order Strongyloidea. This order includes hookworm and threadworms, which are persistent and often debilitating parasites of humans and other vertebrates. The nematode specialist noted that the specimens were not recognizable as an existing known species. Furthermore, the specimen's ability to sexually reproduce, and re-infect the host through multiple generations, was specifically noted by the specialist as an unusual life cycle trait.

Authoritative taxonomic references were also consulted. These references did not contain forms resembling those of the described specimens. [See generally, Anderson, *Nematode Parasites of Vertebrates, Their Development and Transmission* (1992); Ash and Orihel, *Atlas of Human Parasitology* (3rd ed. 1990); Levine, *Nematode Parasites of Domestic Animals and of Man* (1968); and Skryabin et al., *Key to the Parasitic Nematodes: Volume 3, Strongylata* (1992)]. As a result, a new species name, *Cryptostrongylus pulmoni* (n.gen., n.sp.), was assigned to the collected specimens, which were also given the common name "hidden lungworm."

Taxonomic affinities may suggest possible transmission modes for *C. pulmoni* (n.gen., n.sp.). An explanation for sputum association may lie in the observation that *C. pulmoni* (n.gen., n.sp.) belongs to a group of roundworms which infect fruit eating bats and tree shrews (ancestral primates) of Southeast Asia. [See generally, Durette-Desset, "Trichostrongyloid Nematodes and Their Vertebrate Hosts: Reconstruction of the Phylogeny of a Parasitic Group," *Advances in Parasitology* 24:239–307 (1985); and Chabaud, *Sur Les Molineinae Parasites de Mammiferes* (1981)]. Indeed, sputum transmission as an alternative to fecal transmission may have originally evolved in bats whose normal behavior does not provide opportunities for contact with fecal material or contaminated soil.

The indication that *C. pulmoni* (n.gen., n.sp.) evolved as parasites of bats is supported by the existence of its unusual "climber" larva (described supra and depicted in FIG. 1F). This highly specialized and distinctive larva most likely evolved to fulfill a highly specific life-cycle requirement. That requirement is thought to be the need to ascend the vertically aligned esophagus of a hanging bat in order to complete the migration between its respiratory and digestive tracts. This unique requirement arises out of the upside-down roosting posture characteristic of, and exclusive to, bats.

A climber larval form does not appear to be necessary for maintaining human infection for two reasons. First, expulsion of foreign material is a natural function of the human lung. Second, several species of nematodes have unspecialized larvae that are quite capable of traversing the human broncho-tracheal tree. The occurrence of the climber larva as an evolutionary relic which evolved in bats would account for the occurrence of the climber larva in man.

The association with bats is more than just a matter of interest to evolutionary biologists. It should focus public health research on coincident situations, times, and places where humans and bats may have come in contact, perhaps indicating how *C. pulmoni* (n.gen., n.sp.) entered or is maintained within the human population, and suggesting means to sever the connection. Of course, parasite co-occurrences in more than one host species would indicate mutual susceptibility, and the possibility should not be overlooked that a highly mobile species such as man (able to sustain chronic infection) could itself be an important vector of transmission to other animal populations.

D. Comparison with Other Persistent Nematode Infections

Figure 2:
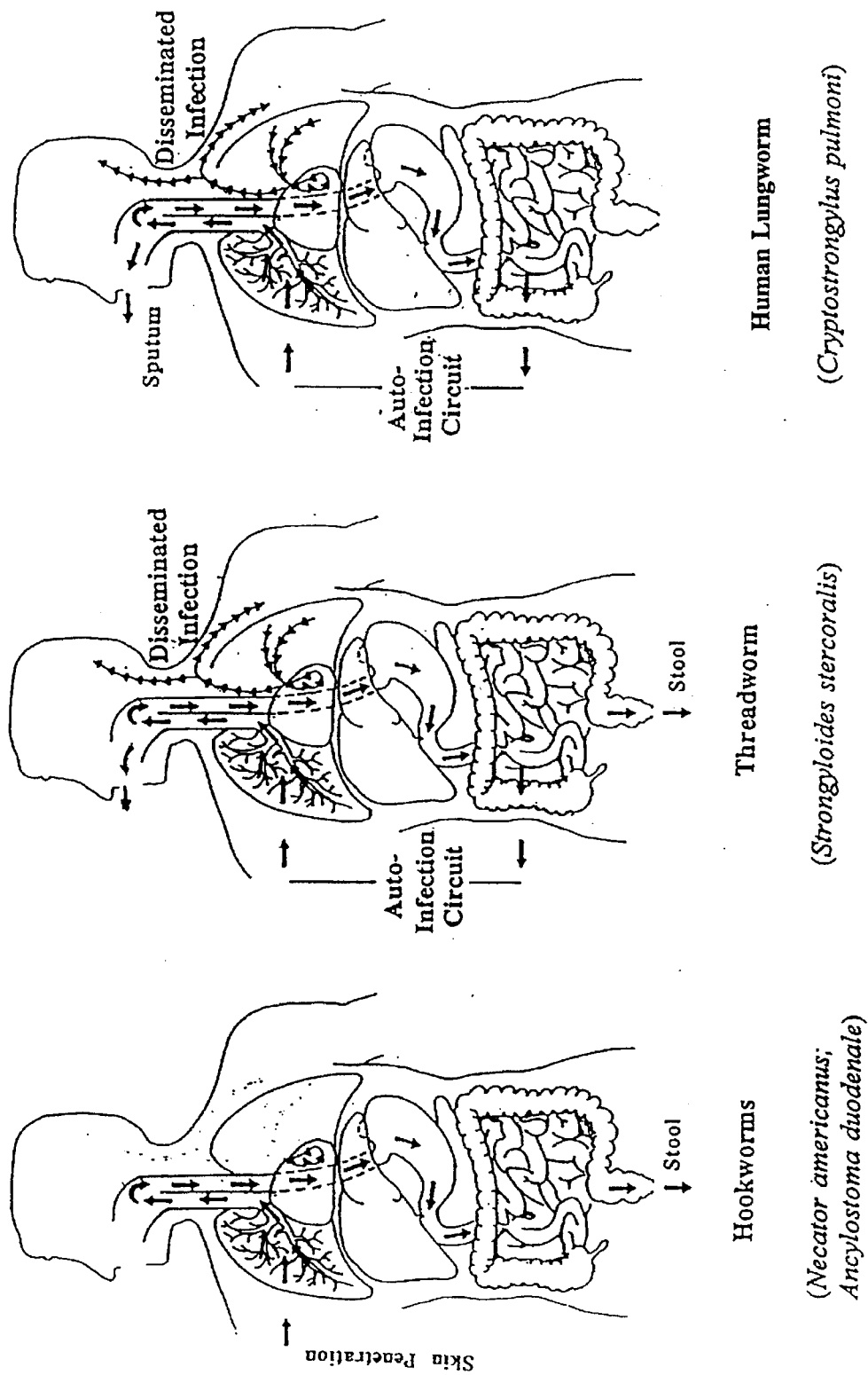

FIG. 2 illustrates the life cycle of human hookworms (*Necator americanus* and *Ancylostoma duodenale*) and threadworm (*Strongyloides stercoralis*) in comparison to the newly identified hidden lungworm (*C. pulmoni* (n.gen., n.sp.)). In hookworm disease, infective filariform larvae from contaminated soil penetrate the skin, most often the skin of bare feet. Upon finding a vein, they are carried by the venous circulation to the right side of the heart. They are then transported through the pulmonary circulation to the lungs, where they bore through the alveolar tissue and enter the bronchial airways. After climbing up the bronchotracheal tree, the larvae are swallowed with sputum in the throat and enter the host's digestive system. Alternatively, larvae can directly enter the digestive track through an oral route following ingestion of contaminated food. Once in the intestine, the larvae attach to and feed on the intestine's epithelial surface and mature into sexual adults.

Sexually produced rhabditiform larvae, non-infective larvae that engage in a free-living cycle usually outside the host, are produced and discharged in the feces. After a few days in the soil environment, rhabditiform larvae molt into filariform larvae, which may then infect other hosts. Unless re-infection from the external environment occurs, infection will last no longer than a single generation. Hookworm infection has, for the most part, been effectively controlled in the United States with anthelmintic agents (e.g., pyrantel pamoate and mebendazole) and with public health education.

Threadworm infection is in many ways an extension and elaboration of the hookworm life cycle, further evolved to increase the duration of host infection. Initial infection follows the general pattern described for hookworms. However, unique adaptations in the threadworm life cycle allow it to re-infect the same host through the previously described autoinfection process. This process involves the production of larvae (through asexual parthenogenesis, a form of nonsexual reproduction, in this species) which mature into the infectious filariform stage while still in the intestine. These infective larvae either bore out of the host's intestine into the surrounding tissues (internal autoinfection) or, after passage through the rectum, bore into the perianal skin (external autoinfection). Once the larvae penetrate a vein, they are transported back into the digestive system via the heart, lungs, tracheal, and esophageal circuit previously described. If the autoinfective route becomes established, multiple generations of threadworms can successfully infect the host. Threadworm infections of several decades and even lifelong infections have been reported (See generally, Liu & Weller, "Strongyloidiasis and Other Intestinal Nematode Infections," Infectious Disease Clinics of North America, Parasitic Diseases 7(3):655–82 (1993)]. As some larvae leave through the feces, stool and culture analysis can detect threadworm disease. However, single stool samples are often negative (approximately 80% of the time) due to the scarcity of fecal larvae in low and moderate level infections; such infections are often detected only after repeated attempts at diagnosis.

Intensive threadworm autoinfection can lead to widespread deposition of larvae, well beyond that of the "normal" respiratory and digestive system routes, into every part of the body. Disseminated infections of this sort occur when larvae enter the arterial circulation and are transported to all tissues via the systemic blood circulation. Intensive autoinfections that lead to widespread dissemination are very dangerous and often fatal. [See Genta, "Global Prevalence of Strongyloidiasis: Critical Review With Epidemiologic Insights into Prevention of Disseminated Disease," Rev Infect Dis 11(2):755–67 (1989)].

*C. pulmoni* (n.gen., n.sp.) has taken the autoinfective process to the extreme. All larvae apparently bore out of the intestine to re-infect the host and give rise to reproductive forms in the lungs. No larvae are found in the stool (as evidenced by the subject's autoinfective skin rashes and negative stool tests), the likely reason why this roundworm has not been discovered heretofore.

A possible rationale exists that explains the selective advantage of giving up fecal transmission as a means of perpetuating the species. This rationale relates to the energetic demands of reproduction. *C. pulmoni* (n.gen., n.sp.) may have taken an evolutionary course where survival was enhanced by conservation in the host (e.g., autoinfection), and highly precise oral transmission of a few larvae rather than wide dispersal of many more larvae in fetes. The end result is an exceedingly small adult form (both in absolute size and relative to the size of its larvae), implying low reproductive output, which has remained hidden to human observers until now. The other chronic human intestinal nematodes, decidedly more "visible" in terms of size and reproductive output, where discovered more than a century ago.

III. Pharmaceutical Preparation and Delivery

A. The Characteristics of Thiabendazole

Specimens of *C. pulmoni* (n.gen., n.sp.) were first recovered following treatment with oral thiabendazole. Thiabendazole is a benzimidazole-derivative anthelmintic agent that is structurally related to mebendazole. [See generally, *AHFS Drug Information* 94, supra]. Thiabendazole has the following chemical structure:

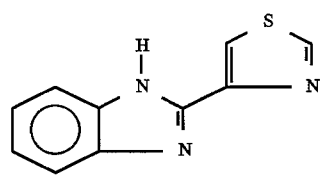

Though not fully elucidated, thiabendazole's mechanism of action likely involves inhibition of the helminth-specific enzyme, fumarate reductase. The agent is effective against most intestinal roundworms that are pathogenic to humans, including hookworms (*Necator americanus* and *Ancylostoma duodenale*) and threadworms (*Strongyloides stercoralis*).

Thiabendazole is rapidly absorbed through the gastrointestinal tract and has also been applied topically to treat certain infections. Thiabendazole is subject to extensive hepatic metabolism, and most of the agent and its metabolites are excreted in urine and feces within 24 hours of administration. The drag has a $pK_a$ of 4.7 and it is commercially available in both a tablet and a suspension; the suspension has a pH of 3.4–4.2. [See *AHFS Drug Information* 94, supra].

The adverse effects of thiabendazole are many, and up to one-third of patients receiving the drug in recommended doses experience at least one adverse effect. Thiabendazole's adverse effects are well known. [See, e.g., *Physicians' Desk Reference*, 45th Ed. (1991); *AHFS Drug Information*

94, supra]. The most common adverse effects include nausea, vomiting, and dizziness; less frequent adverse effects include paresthesia, psychic disturbances, and altered hepatic enzymes.

It is not uncommon for a recipient of an anthelmintic to expel roundworms from the nose and the mouth. For example, patients being treated with thiabendazole for ascariasis have experienced live worms in their mouths and noses. [See, e.g., AHFS Drug Information 94, supra]. Furthermore, even prior to administration of an anthelmintic, examination of the sputum of an individual suspected of having a roundworm infection may sometimes assist in diagnosis if that infection entails pulmonary manifestations; for instance, S. stercoralis larvae may sometimes be identified in one's sputum if the pulmonary system is involved. [See Medical Microbiology—An Introduction to Infectious Diseases, Ch. 49, supra]. However, there has never been a published report of a sputum sample containing C. pulmoni (n.gen., n.sp.).

B. Administration of Oral Thiabendazole

The subject undertook a therapeutic trial with oral thiabendazole that involved a dose of approximately 1.5 grams per day over a five-day period; this therapeutic trial was for the treatment of a presumptive S. stercoralis infection, the presence of which could subsequently not be confirmed. The subject reported several significant, and at times severe, responses to this treatment. In addition to the nausea and confusion which are common with thiabendazole, other symptoms suggested the presence of a disseminated roundworm infection. Such symptoms included strong focal itching in conjunction with the appearance of small blood spots on the face, legs, and neck. The blood spots suggest that oral drug therapy may have caused dispersed larvae to penetrate the host's skin.

Severe abdominal pain, thirst, and abdominal bloating on the fourth day of treatment was followed two days latter with the expulsion of dark brown, almost black, copious stools over the next several days. The tough elastic nature of the stool material, which resisted tearing when it was probed, along with the color of aged intestinal blood, suggests that it was actually part of the intestinal lining which was expelled as a result of the severe inflammatory reaction associated with oral thiabendazole treatment. Expulsion of portions of the epithelial lining of the gut has been reported for other roundworm infestations of the intestinal mucosa. [See generally, Klein The Parasites We Humans Harbor, Ch. 3 (1981)]. The subject also coughed up large amounts of frothy sputum during the last days of treatment, suggesting that the lungs were also infected. The sputum was not examined, as S. Stercoralis was believed to be the infective gent.

Following these expulsion type reactions, the subject was completely symptom-free until a minor relapse of fatigue two weeks later. A major attack involving prolonged fatigue and gastrointestinal pain and bloating occurred two weeks after the first minor re-occurrence.

An oral dosing regimen of 3 g of thiabendazole per day for 7 days (the recommended dose for treating disseminated strongyloidiasis) was eventually administered under the care of an infectious disease specialist. However, the subject experienced debilitating side effects following that oral regimen. In addition, orally administered thiabendazole did not effectively control the subject's infection, which was latter determined not to be caused by S. stercoralis (through Strongyloides IgG antibody testing). As a result, other means of identifying the subject's infection were ultimately sought. These resulted in the aerosolized method, described infra, for the diagnosis of C. pulmoni (n.gen., n.sp.) infections.

It should be noted that C. pulmoni (n.gen., n.sp.) has also been recovered from the sputum of a member of the subject's household using the method described below. However, the household member had been virtually asymptomatic until the twelve months prior to isolation of C. pulmoni (n.gen., n.sp.) in the household member's sputum. All references to "the subject" are to the 50 year old male previously described.

Interpreted in the light of the now apparent C. pulmoni (n.gen., n.sp.) infection, the aforementioned observations offer important insights for directing further treatment. First, orally administered thiabendazole is potentially dangerous, and does not appear to kill all forms of C. pulmoni (n.gen., n.sp.). Second, re-infection is apparently possible within two weeks, which may represent the minimal interval between successive generations of the parasite.

C. Administration of Aerosolized Thiabendazole

The development of an aerosol device and method for dispensing thiabendazole as a mist for inhalation proved much more promising. This technique consistently produced sputum samples containing specimens of C. pulmoni (n.gen., n.sp.). Furthermore, trials with the aerosol preparation of inhaled thiabendazole, at low total body doses, killed C. pulmoni (n.gen., n.sp.) in the lungs with minimal adverse effects (which included moderate fatigue and some heaviness in the chest). Moreover, as will be presented in more detail below, the subject's clinical symptoms also markedly improved.

The subject administered doses by inhalation; these doses were substantially less than the total daily recommended oral dose of thiabendazole. The recommended oral dose of thiabendazole is 25 mg/kg for patients weighing less than 70 kg, usually administered twice daily (i.e., 50 mg/kg/day). For patients weighing more than 70 kg, the recommended dose is 1.5 g; the maximum recommended daily dose is 3 g. Due to limited experience in children weighing less than about 13 kg, the drug is generally not administered to such children unless the benefits will likely outweigh the possible risks. [See AHFS Drug Information 94, supra, pp. 50–52 (1993)]. Doses ranging between approximately 4–7% of the total daily oral dose (50 mg/kg) of thiabendazole are administered. Taking into consideration that pediatric precautions are usually followed for children weighing less than about 13 kg and that the maximum daily dose is 3 g, the 4–7% amount corresponds to a daily dose ranging between approximately 25 mg and 210 mg. It may be desirable to administer 5% of the total daily oral dose because of both the ease in remembering this conversion factor and in actually converting the oral dose to the appropriate inhaled dose; the 5% amount corresponds to a daily inhaled dose ranging between approximately 35 mg and 150 mg.

An acidic solution of thiabendazole (Mintezol®, obtained by prescription) is prepared by dissolving thiabendazole tablets in sterile water, or similar diluent, and an acid. An acidic solution of about a pH of 4.0 enhances thiabendazole's solubility. The acid may be hydrochloric acid, citric acid, acetyl salicylic acid, or another acid, though hydrochloric acid may be preferable because of the stability of the solution formed with that acid. The final concentration of thiabendazole ranges between approximately 1.0 mg/ml and 2.0 mg/ml. More or less concentrated solutions can also be prepared and administered. The present invention contemplates the use of methods to enhance the solubility of thiabendazole. For example, thiabendazole may be chemically modified to improve its solubility; one such method might entail the covalent bonding of a functional group highly soluble in aqueous solution.

The calculated dose is placed into a nebulizer equipped with a breathing tube. Next, one or more small test doses are inhaled to ensure that there are no allergic or other adverse reactions. If the test doses are tolerated, the remainder of the calculated dose is inhaled. The duration of time required for inhalation of the total dose is dependent on a number of factors, including the concentration of the solution and the total dose to be administered. Following inhalation of the thiabendazole, an expectorant, e.g., Robitussin® brand of guaifenesin (obtained over-the-counter), may be administered to aide in the expulsion of C. pulmoni (n.gen., n.sp.) for diagnostic purposes.

As alluded to previously, the subject's symptoms greatly improved following aerosolized administration of thiabendazole. Specifically, when inhalation treatments were administered at approximately weekly intervals over a three-month period, the subject's condition improved such that he no longer suffered from severe gastrointestinal symptoms like cramping and diarrhea. Furthermore, there was a cessation of prostrating attacks of fatigue, malaise, and general pain that previously would last several days. Moreover, bouts of fatigue became much less frequent, noticeably shorter, and less intense. In summation, the subject reported that his quality of life markedly improved subsequent to aerosolized administration of thiabendazole.

A detailed description of the preparation and administration of thiabendazole for inhalation is described in the Experimental section, Example 2, infra. It should also be noted that the invention contemplates the use of other anthelmintics; thus, agents like mebendazole, pyrantel pamoate, and various botanicals that have an anti-parasitic effect when administered orally are expected to be effective against C. pulmoni (n.gen., n.sp.) in an inhalation form and are also contemplated by the present invention. The botanicals include Artemesia, which is sold over-the-counter as a food supplement. Furthermore, newer agents like albendazole and ivermectin (Mectizan®; 22,23-dihydroabamectin) may also prove to be effective against C. pulmoni (n.gen., n.sp.) when administered by inhalation.

Administration of thiabendazole in an inhalation form was found to be much more useful than oral thiabendazole for diagnosing and treating C. pulmoni (n.gen., n.sp.) infection.

From a therapeutic standpoint, inhaled thiabendazole did not produce larval penetration of the skin as did the oral form. Hence, the possibility of re-infecting the host or spreading the disease to others is significantly reduced. In addition, as the dose for inhalation is much less than the oral dose, the adverse effects associated with inhalation treatment are concomitantly reduced in both number and degree. As a result, the subject was able to take the inhaled medication at weekly intervals, a dosing regimen that would not have been possible with the oral form. Because the parasite can reproduce in the host and its larvae can re-infect the host, repetitive treatment at an interval less than the generation time is needed to receive significant and lasting therapeutic results. Recurrence of the subject's symptoms at about two-week intervals implies that the organism has a generation time of at least two-weeks.

As is evident from the foregoing discussion, inhalation of thiabendazole is much more useful than administration of oral thiabendazole for diagnosing the presence of C. pulmoni (n.gen., n.sp.), is better tolerated than the oral preparation, and results in significant improvement of the clinical symptoms associated with C. pulmoni (n.gen., n.sp.) infections.

IV. Potential Clinical Manifestations of Human C. Pulmoni (n gem., n.sp) Infection Chronic Fatigue Syndrome (CFS), an often debilitating illness with unknown etiology, has been reported in many developed countries beginning in the early 1980's. The development of CFS criteria is a recent attempt to systematically organize and describe a constellation of symptoms and findings (mostly exclusionary) which may be related to, or indeed synonymous with, a number of conditions variously reported in both medical and popular accounts; theses conditions include benign myalgic encephalomyelitis (ME), fibromyalgia (FM), neurasthenia; chronic fatigue immune dysfunction syndrome (CFIDS), candida hypersensitivity, total allergy syndrome, environmental illness, and other poorly understood conditions which appear to reflect a disturbed immune response.

Parasitic infection is one of the conditions which should be excluded before a diagnosis of Chronic Fatigue Syndrome is made according to the U.S. Center for Disease Control's published criteria. [See Holmes, et al., "Chronic Fatigue Syndrome: A Working Definition," Ann Intern Med 108:38714 89 (1988)]. Because extensive stool testing in CFS patients has failed to uncover nematode eggs or larvae, roundworm infections have not previously been thought to be a plausible causal agent of CFS. With the discovery of C. pulmoni (n.gen., n.sp.), whose unique life cycle does not result in the deposition of eggs or larvae in expelled feces, that reservation should no longer apply. Indeed, comparisons of symptoms and clinical and research findings suggest that roundworm infections in general, and C. pulmoni (n.gen., n.sp.) infection in particular, have many features in common with CFS.

The subject's illness meets the criteria for Chronic Fatigue Syndrome. Initially, roundworm infections are characterized by relapsing chronic fatigue with eosinophilia. [See Hegner et al., Outlines of Medical Zoology, (1927)]. The namesake of CFS is, of course, chronic fatigue, one of the primary characteristics of the subject's illness. During the subject's bouts with flu-like attacks, the subject also has mildly elevated eosinophilia. Many CFS patients have allergies. Low-grade eosinophilia is characteristic of both allergies and, in some cases, chronic roundworm infection. [See Bell, The Doctors Guide to Chronic Fatigue Syndrome, (1994)]. Similarly, CFS sufferers often have a mild elevation of hepatic enzymes. [See Berne, Running On Empty: Chronic Fatigue Immune Dysfunction Syndrome, (1992)]. The subject also has elevated hepatic enzyme levels.

Next, many of the gastrointestinal symptoms associated with CFS are analogous to those caused by C. pulmoni (n.gen., n.sp.). Filariform larvae boring out of the intestine can penetrate the liver and other abdominal organs in autoinfective nematode disease. [See Poltera & Katsimbura, "Granulomatous Hepatitis Due to Strongyloides Stercoralis.," J Path 113:241–46 (1973)]. As previously noted, C. pulmoni (n.gen., n.sp.) larvae in the gut appear to be exclusively autoinfective, and tissue penetration by migrating larvae could account for the prominence of gastrointestinal symptoms, abdominal pain, tenderness, and swelling which are commonly reported in CFS. [See Bell, supra].

Additionally, roundworms appear to secrete a substance which reduces the host's ability to form new lymphocytes in response to mitogenic agents. Of note, analogous factors which suppress lymphocyte proliferation in response to mitogens have been reported in CFS. [See, e.g., Lloyd et al., "Immunological Abnormalities in the Chronic Fatigue Syndrome," Med J Aust 151(3):122–4 (1989); and Klimas et al., Immunological Abnormalities in the Chronic Fatigue Syndrome," J Clin Microbiol 28: 1403–10 (1990)].

Research on CFS has shown a high degree of variations in cytokine and lymphocyte types, including at times inconsistent and even contradictory findings. [See generally, Yunus, *Chronic Fatigue Syndrome and Fibromyalgia: Similarities and Differences*, Pub. CFIDS Ass Am, Charlotte, N.C., 7 pps (1994); Klimas et at., supra; and Bell, supra]. Such variable patterns might reasonably be explained by the presence of a chronic infective agent, like a roundworm, which is capable of misdirecting the host's immune response. Roundworms are known to secrete cytokine-like substances which may affect the host's immune response. [See, e.g., *Immunology and Molecular Biology of Parasitic Infections*, Kenneth S. Warren ed., Ch. 19 (1993)]. So for example, changing levels of specific lymphocyte types and cytokines might reasonably be explained by whether the parasite or host is winning the battle for control of the immune response, at the time measurements are being made.

The tendency for allergic persons to produce high levels of IgE is suspected by some nematologists to predispose them toward roundworm infections.

From about 60–80% of CFS patients have a history of pre-existing allergies. Also, allergic reactions are reported by many patients to worsen significantly after the onset of CFS. Roundworm infections are known to produce allergic-type reactions in human hosts.

The similarities outlined above justify the evaluation of persons with CFS, or multiple allergies of unclear etiology, for the presence of *C. pulmoni* (n.gen., n.sp.) or other possible roundworm parasites with a similar hidden life cycle. At minimum, it would seem prudent to be aware of the signs of accelerating autoinfections in persons with CFS-type illnesses who are receiving prolonged treatments which could suppress the immune response.

Species in the family to which *C. pulmoni* (n.gen., n.sp.) belongs typically infect more than one host organism. As such, household pets and farm animals should also be investigated as potential carriers. If this parasite occurs in farm animals, raw or under cooked meat and unpasteurized dairy products would have to be evaluated as possible sources of infection. Runimants (e.g., cows, sheep, and goats) harbor a family of roundworms only slightly removed from those that parasitize primates and bats. [See Durette-Desset, supra].

Experimental

In the disclosure which follows, the following abbreviations apply: ml (milliliters); kg (kilograms); g (grams); mg (milligrams); mm (millimeters); n.gen. (new genus); n.sp. (new species); ME (myalgic encephalomyelitis); FM (fibromyalgia); CFIDS (chronic fatigue immune dysfunction syndrome); CFS (chronic fatigue syndrome); MSD (Merck Sharpe & Dohme; West Point, Pa.); Janssen (Janssen Pharmaceutica, Inc., Piscataway, N.J.); Pfizer (Pfizer Inc., New York, N.Y.); Hankscraft (DeVildiss Health Care, Inc., Somerset, Pa.).

The following examples serve to illustrate certain preferred embodiments and aspects of the present invention and are not to be construed as limiting the scope thereof.

EXAMPLE 1

Sampling Methods and Analysis

Samples of sputum and stools were taken from the subject in conjunction with treatment with the anthelmintic drug thiabendazole. Thiabendazole (Mintezol®, obtained by prescription) was administered in two treatment regimens over the sampling period. The first regimen entailed 1,500 mg/day for one day only; the second regimen, begun one week later, consisted of 2,300 mg/day for four days. The total daily dose was divided and administered in approximately equal doses three times daily.

Sputum samples were preserved in formalin, stained with iodine stain and examined microscopically. Stool samples were divided into two portions. One portion was preserved in formalin in a 1:2 ratio of stool-to-preservative. 20 ml of each of the formalin-preserved stool samples were examined microscopically for the presence of parasites. The other stool sample portion (approximately 1 g of fresh stool) was placed in a nutrient-filled petri dish. These stool sample cultures were examined microscopically two days later for the presence of parasite larvae; this microscopic procedure has been recognized as being highly sensitive for the detection of threadworm larvae. [See Koga et al., "A modified agar plate method for detection of *Strongyloides stercoralis*," Am J Trop Med Hyg 45(4):518–21 (1991)].

Eight stool samples were taken concomitant with the second regimen of thiabendazole treatment. No evidence of worm parasites was detected by either direct microscopic examination or by stool culture.

Twelve sputum samples were taken over a two-week period prior to the first administration of thiabendazole. All were negative. A twenty-four hour sputum sample, begun immediately after thiabendazole treatment, yielded the specimens shown in FIGS. 1A and 1F (The specimens depicted in FIGS. 1B, 1C, and 1D were recovered after the development of an aerosol inhalant to deliver the thiabendazole, the aerosol delivery vehicle being described in Example 2, infra).

EXAMPLE 2

Aerosol Delivery System For Diagnosing And Treating Human Lungworm Infection

Thiabendazole tablets (Mintezol®, obtained by prescription) were dissolved in warm, sterile filtered water which was slightly acidified (to enhance solubility) with citric acid to produce a solution of 1.0 mg thiabendazole per ml (pH of the solution was about 4.0). The solution was loaded into a centrifugal nebulizer (Hankscraft cool mist humidifier, model 240D) fitted with a breathing tube, and administered as an inhaled mist.

An effective dose equivalent to 5% of the recommended oral daily dose of thiabendazole was administered. For the 70 kg subject, the inhaled dose of thiabendazole was 150 mg, calculated as follows:

inhaled dose=5% of total daily oral dose
  inhaled dose=5% (50 mg/kg×70 kg)
  inhaled dose=5% (3500 mg)
  inhaled dose=5% (3000 mg) [3.0 g is maximum recommended daily dose]
  inhaled dose=150 mg The dose was divided and administered over several intervals of different durations. Initially, two 1-minute inhalation sessions were administered at a 20 minute interval to check for tolerance and the possibility of adverse reaction. As no adverse effects were noted, the remaining dose was administered over intervals of increasing duration until the entire 150 ml of solution (1 mg thiabendazole/1 ml solution) was inhaled. Specifically, a 3-minute inhalation was administered about thirty minutes after the later 1-minute inhalation; this was followed by a 5-minute inhalation about 4 hours later, then a 10-minute inhalation about twenty minutes later, and finally a 30-minute inhalation about two hours later.

Following this treatment, Robitussin® brand of guaifenesin (obtained over-the-counter), an expectorant, was administered to assist in expulsion of any organisms. Two sputum samples were collected at 12-hour intervals and each was preserved in an approximately equal volume of 20% formaldehyde-buffered saline solution immediately following collection. The preserved samples were iodine-stained and microscopically examined in a drop-by-drop manner, under a cover slip, for the presence of roundworms.

The first sputum sample produced all of the specifically recognizable forms of *C. pulmoni* (n.gen., n.sp.) which are present in the lungs (i.e., males, females, first-stage larvae, and second-stage larvae). The second sputum sample, collected 12 hours after the first, contained several hundred objects of the size and shape of, and are thought to be the necrotic remains of, *C. pulmoni* (n.gen., n.sp.) specimens.

As set forth in detail above, the subject experienced therapeutic benefit following inhalation treatment with thiabendazole. In summary, there was a cessation of the subject's severe gastrointestinal symptoms and prostrating attacks of fatigue, malaise, and general pain that previously would last several days.

EXAMPLE 3

Inhalation Treatment Regimen

A first diagnostic test consists of a 10 minute initial tolerance trial, followed by a 10 minute rest to evaluate for possible acute adverse effects; such effects include hypersensitivity reactions to the drug, like anaphylactic reactions.

In the absence of acute adverse effects, the remainder of the therapeutic dose (as calculated in Example 2, supra) is administered. The patient should be monitored for adverse effects for at least a twenty minute period after the administration of the therapeutic dose. This monitoring period should be applied to both the initial treatment and any treatments which are administered thereafter.

From the above, it should be evident that the present invention provides for a method of diagnosing a heretofore unrecognized microscopic roundworm, *C. pulmoni* (n.gen., n.sp.), and to a rational method of treating that organism. The present invention is clearly needed to help isolate and eradicate *C. pulmoni* (n.gen., n.sp.), an extremely debilitating organism whose unique life cycle has prevented its discovery until now.

I claim:

1. A method of diagnosing the presence of roundworms in lungs, comprising the steps of:

(a) providing i) a subject suspected of being infected with *Cryptostrongylus pulmoni* and ii) aerosolized thiabendazole for inhalation in a daily dose ranging between approximately 25 mg and 210 mg;

(b) administering said aerosolized thiabendazole by inhalation to said subject, (c) collecting sputum samples from said subject following said administering; and (d) analyzing said sputum samples for the presence of said *Cryptostrongylus pulmoni* in the lungs of said subject.

2. The method of claim 1 wherein said *Cryptostrongylus pulmoni* is present in the lungs of said subject.

3. The method of claim 1 wherein said thiabendazole is administered in a daily dose ranging between approximately 35 mg and 150 mg.

4. A method of diagnosing the presence of roundworms in the lungs, comprising the steps of:

(a) providing i) a subject suspected of being infected with roundworms and ii) a composition for inhalation consisting essentially of aerosolized thiabendazole;

(b) administering said aerosolized thiabendazole in a daily dose ranging between approximately 25 mg and 210 mg by inhalation to said subject;

(c) collecting sputum samples from said subject following said administering; and (d) analyzing said sputum samples for the presence of *Cryptostrongylus pulmoni* in the lungs of said subject.

5. The method of claim 4 wherein said thiabendazole is administered in a daily dose ranging between approximately 35 mg and 150 mg.

6. The method of claim 4 wherein said roundworms are present in the lungs of said subject.

* * * * *

UNITED STATES PATENT AND TRADEMARK OFFICE
CERTIFICATE OF CORRECTION

PATENT NO. : 5,645,819
DATED : July 08/1997
INVENTOR(S) : Dr. Lawrence A. Klapow It is certified that error appears in the above-indentified patent and that said Letters Patent is hereby corrected as shown below:

In col. 4, line 28, please delete "C *pulmoni*" and insert --C. *pulmoni*--.
In col. 7, line 18, please delete "," after the word "large".
In col. 10, line 21, please delete "fetes" and insert --feces--.
In col. 14, line 18, please delete "108:38714 89" and insert --108:387-89--.
In col. 15, line 4, please delete "et at." and insert --et al.--.

Signed and Sealed this

Thirtieth Day of December, 1997

Attest:

BRUCE LEHMAN

Attesting Officer

Commissioner of Patents and Trademarks